(12) United States Patent
Attar et al.

(10) Patent No.: US 7,553,450 B2
(45) Date of Patent: Jun. 30, 2009

(54) IRREVERSIBLE HUMIDITY EXPOSURE DOSE INDICATOR DEVICE

(75) Inventors: Amir J. Attar, Raleigh, NC (US); Dan Edward Stark, Raleigh, NC (US)

(73) Assignee: Appealing Products, Inc., Raleigh, NC (US)

( * ) Notice: Subject to any disclaimer, the term of this patent is extended or adjusted under 35 U.S.C. 154(b) by 0 days.

(21) Appl. No.: 11/621,005

(22) Filed: Jan. 8, 2007

(65) Prior Publication Data

US 2008/0163673 A1 Jul. 10, 2008

(51) Int. Cl.
*G01N 1/00* (2006.01)
*G01N 33/00* (2006.01)
(52) U.S. Cl. .............. 422/58; 422/55; 436/41; 436/130; 436/165; 436/111; 73/73; 73/335.01; 116/200
(58) Field of Classification Search .......... 422/58, 422/55; 356/347; 116/206; 252/408, 174.25; 73/335, 73; 436/165, 41, 130, 111
See application file for complete search history.

(56) References Cited

U.S. PATENT DOCUMENTS

| | | | |
|---|---|---|---|
| 2,214,354 A * | 9/1940 | Snelling | ............... 116/206 |
| 2,249,867 A | 7/1941 | Snelling | |
| 2,460,065 A | 1/1949 | Davis | |
| 2,460,066 A | 1/1949 | Davis | |
| 2,460,067 A | 1/1949 | Davis | |
| 2,460,070 A | 1/1949 | Davis | |
| 2,460,071 A | 1/1949 | Davis | |
| 2,460,072 A | 1/1949 | Davis | |
| 2,460,073 A | 1/1949 | Davis | |
| 2,460,074 A | 1/1949 | Davis | |
| 2,526,938 A | 10/1950 | Davis et al. | |
| 2,580,737 A | 1/1952 | Davis | |
| 2,627,505 A | 2/1953 | Goodwin et al. | |
| 2,716,338 A | 8/1955 | Blinn | |
| 3,084,658 A | 4/1963 | Schell | |
| 3,200,387 A * | 8/1965 | Loscher | ............... 96/417 |

(Continued)

*Primary Examiner*—Walter D Griffin
*Assistant Examiner*—Christine T Mui
(74) *Attorney, Agent, or Firm*—Steven J. Hultquist; Intellectual Property Technology Law

(57) ABSTRACT

An irreversible humidity exposure dose indicator device, including a housing sealed at a first end thereof and adapted at a second end thereof to admit ambient gas ingress into an interior volume containing chromogenic material. The chromogenic material in contact with water irreversibly absorbs such water to produce a change whose extent is correlative of cumulative exposure of the device to humidity. The device may be configured as an indicator card including an intermediate permeable membrane coated on a first side thereof with a layer of a deliquescent solid and being in contact on a second side thereof with a layer containing a reactive indicator, with a water-permeable layer adjacent to the layer containing the deliquescent coating, enclosed within a water-impermeable transparent enclosure. The device can include an opening to the permeable layer that is shielded by a removable member that is removed to initiate the dosimetric process, and permit water vapor to diffuse through the opening and liquefy the deliquescent material, so that the liquid permeates through the membrane and a visible indication of the location of the wet front is seen as the water contacts the chromogenic material. A scale can be printed on the exterior of the enclosure to permit a viewer to see the progress of the indication, e. g. of a color front.

28 Claims, 3 Drawing Sheets

U.S. PATENT DOCUMENTS

| | | |
|---|---|---|
| 3,680,384 A | 8/1972 | Carrier |
| 3,898,172 A * | 8/1975 | Reif et al. ............... 252/408.1 |
| 4,034,609 A | 7/1977 | Fuller |
| 4,050,307 A | 9/1977 | McMullen et al. |
| 4,098,120 A | 7/1978 | Manske |
| 4,150,570 A | 4/1979 | Fuller |
| 4,321,157 A * | 3/1982 | Harris et al. ............... 510/348 |
| 4,666,859 A | 5/1987 | Attar |
| 4,772,560 A * | 9/1988 | Attar ......................... 436/165 |
| 4,793,180 A | 12/1988 | Stewart et al. |
| 4,840,919 A | 6/1989 | Attar |
| 4,854,160 A | 8/1989 | Glatt |
| 5,194,224 A * | 3/1993 | Plotz et al. .................... 422/55 |
| 5,224,373 A | 7/1993 | Williams et al. |
| 5,727,498 A * | 3/1998 | Hackler et al. ............. 116/206 |
| 6,698,378 B1 | 3/2004 | Dick et al. |
| 6,947,138 B2 * | 9/2005 | Arno ......................... 356/437 |
| 7,277,019 B2 | 10/2007 | Povenmire |

\* cited by examiner

IRREVERSIBLE HUMIDITY EXPOSURE DOSE INDICATOR DEVICE

FIELD OF THE INVENTION

The present invention generally relates to humidity dosimetry, and more specifically to an irreversible humidity exposure dose indicator card for ready determination of the humidity exposure history of a monitored article or environment. A new class of irreversible humidity indicator cards is described herein, which are quantitative and which do not contain a dye. The cards measure quantitatively the integrated exposure dose to humidity and not only the current or contemporary relative humidity. The color-based indication of the cumulative humidity exposure enables an easy observation of the progress of a front of color change.

BACKGROUND OF THE INVENTION

When shipping or storing many types of materials, particularly electronic components, it is desirable to know whether those components have been exposed to a particular dose or amount of humidity, since exposure to excessive humidity can cause damage to those components. For example, electronic components can be damaged by exposure to even low levels of humidity and even where the exposure is only for short periods of time. Mounting to a printed circuit board of even a single electronic component that has been exposed to excess humidity can damage the entire board. Electronic components can also be contaminated and/or damaged by exposure to ambient gases, dust and other particulate matter that may be carried to electronic components by atmospheric water vapor particles.

Due to this moisture sensitivity, various humidity indicators have been developed to help users quantitatively assess the integrated cumulative dose of humidity to which a part or article has been exposed, e.g., outside or inside a shipping or storage container.

There are three general classes of humidity indicators. One class of humidity indicators is constituted by reversible humidity indicators (RHIs) that change their color upon exposure to specific humidity levels. Such RHIs typically utilize cobalt chloride as the humidity indicator material. Cobalt chloride changes color when exposed to predetermined levels of humidity and returns to its original color when the humidity level drops below that predetermined level. RHIs can be used to indicate the current condition of a desiccant and/or the current humidity level within a storage container.

Irreversible maximum humidity indicators (MHIs) are a second type of humidity indicator. MHIs indicate if a predetermined level of humidity was reached even for a short period, and can be used, for example, inside a storage container. This indication will not change even if the level of humidity drops below the predetermined level when checked at a later time. Large changes in humidity levels may be experienced by storage containers when they are used in relatively warm climates characterized by dramatic rises and falls in moisture level depending on the temperature of the surrounding air, particularly when an article is packed in a cold environment and moved through warmer climates. This phenomenon may be encountered by materials with different humidity sorption or storage characteristics in the same container. Under such highly variable humidity conditions, a RHI might fail to indicate the temporary presence of high humidity within a storage container even though such high humidity may have been sufficient to cause damage to the components present in the storage container.

The third type of humidity indicator is an irreversible humidity dose indicator (HDI). An HDI displays a measure of the time integral of the level of humidity, H, to which an item was exposed, in accordance with the equation:

$$D = \int H^* dt \qquad (1)$$

in which D is the humidity dose, and t is time. The humidity dose to which a part, a drug or food has been exposed is typically what causes them to deteriorate, whether they are in a package or unpackaged. Therefore, the humidity dose is a most accurate measure of the cause of the deterioration of materials. Even if the part is stored in a hermetically sealed package, the humidity changes inside the package due to changes in the temperature and differences in the sorption energy of water on different surfaces within the container. An HDI provides a quantitative cumulative measure of the humidity exposure. Use of an HDI gives the user a better measure of the cumulative deterioration of a stored item. This is a very important measure when storing items such as electronic parts, drugs, artillery shells, missiles, etc, particularly when the structure or packaging includes metal constituents. Such metal structure or packaging is corroded faster at greater humidity, and the total corrosion relates to the integral dose of humidity to which the metal was exposed. The indication of the HDI continues to increase even if the level of humidity drops, since it represents an integrated value.

One of the first MHI devices was disclosed in U.S. Pat. No. 2,214,354, which describes the use of a calcium chloride material that is mixed with a water soluble dye and deposited on a porous surface material, such as a sheet of absorbent paper. Upon exposure of the absorbent sheet to a predetermined humidity level, the calcium chloride material liquefies and releases the dye in liquid form. The dye then is carried by capillary action onto the porous surface of the absorbent paper, where it produces a permanent and irreversible dye mark. This patent also describes various deliquescent agents that may be employed to indicate different humidity levels.

To maintain a consistently low humidity level, shipping containers and long term storage containers usually contain desiccant materials. These desiccant materials dehydrate the storage area and are intended to maintain the humidity level within that storage area at a predetermined low level. These containers are periodically opened to recharge or replace the desiccant materials placed within the container and/or to check the level of humidity in the storage container. After replacing the desiccant material, the container is again sealed. In order to determine whether the humidity level in these storage containers has ever reached certain critical levels, MHIs are also frequently placed within the containers together with the desiccant materials. These MHIs can be viewed at the same time that the desiccant material is being checked to determine whether a harmful humidity level has ever been reached in the shipping container.

Various RHIs, utilizing different deliquescent salts, are disclosed in a series of patents that issued in the 1940's and 1950's including U.S. Pat. Nos. 2,460,065; 2,460,066; 2,460,067; 2,460,068; 2,460,069; 2,460,070; 2,460,071; 2,460,072; 2,460,073; 2,460,074; 2,526,938; 2,580,737; and 2,627,505. Some RHI cards are capable of showing different levels of humidity on the same card by use of a series of different deliquescent agents that change color at varying humidity levels, as disclosed in U.S. Pat. No. 2,249,867.

Humidity indicator sheets and cards that contain deliquescent salts and dyes have commonly been used to detect the relative humidity level present within storage containers. See for example, U.S. Pat. Nos. 2,249,867; 4,034,609; 4,150,570; and 4,854,160. Button-type humidity indicators or "plug" humidity indicators are also sometimes used with packaging material and are disclosed, for example, in U.S. Pat. Nos. 2,716,338; 3,084,658; and 4,050,307. Another device for monitoring humidity levels, particularly in poured cement, is disclosed in U.S. Pat. No. 3,680,364.

A multiple layer, reversible humidity sensing device containing a reflective layer, which is useful in viewing changes in color of a humidity indicator card, is disclosed by U.S. Pat. No. 4,034,609.

A reversible humidity indicator card contained within transparent, flexible sheet materials with an impermeable front layer is disclosed in U.S. Pat. No. 5,224,373. This humidity indicator card is specifically designed for utilization with an electronic meter that can "see" the color changes through a "window" in a barrier bag.

A delayed action MHI card is disclosed in U.S. Pat. No. 4,793,180.

All MHI cards hitherto known are based on combinations of deliquescent salts and water-soluble dyes. In order to prepare humidity indicator cards that react at various humidity levels, different combinations of deliquescent salts and dyes must be chosen. Only cards that show the same change in color at each chosen humidity level are acceptable to users of these cards. Otherwise, if there are varying color changes, it may be difficult to determine whether a specific humidity level has been reached. W. B. Abel: Chemical Maximum Humidity Indicator Update Report, BDX-613-1989 and U.S. Pat. No. 3,898,172 teach that only certain combinations of salts and dyes are useful for this purpose, since the dye is quite soluble in the saturated salt solution that is formed upon deliquescence. In addition, the solubility and color of the dye must be independent of pH changes that may be attributed to the deliquescence of the salt. To ensure a proper shelf-life of the indicator card, the dye also must not react with the salt in any way (e.g., by redox reaction, or acid-base reaction). It is quite difficult to use either the same dye or different dyes with the same color and different salts over the entire humidity spectrum.

Mixing the individual salts with the dye is an additional required step for the production of the previously known MHIs. If the chosen salt and dye have different particle sizes, inhomogeneous distribution of the dye in the salt may occur and lead to inhomogeneous color and appearance on the indicating spot of the humidity indicator. This problem can be overcome by milling the salt and dye together, but this is not possible for all salt-dye combinations, especially if the salt already holds water of crystallization.

Few HDIs have been disclosed in the patent or the open literature. One of the most important HDIs is disclosed in U.S. Pat. No. 4,098,120 (assigned to Minnesota Mining and Manufacturing Company). This patent describes a cumulative humidity indicating device that visibly indicates the total exposure to humidity. The device of this patent comprises, in combination, a deliquescent compound, a liquid absorbent wick, and an indicating means. The liquefaction of the deliquescent compound when it absorbs water at a particular humidity level allows it to wick. The progress of the liquid front through the wick indicates the integrated amount of humidity that has been absorbed, above the absorption threshold of the deliquescent material.

SUMMARY OF THE INVENTION

The present invention relates to a new class of structures of HDI that (i) provide a quantitative indication of the exposure dose, (ii) are highly flexible in terms of design so they can be used in different applications that require measuring different ranges of humidity doses, (iii) are of a low-cost character, (iv) do not require a power source and (v) yield results that are very simple to use, read and understand.

In addition, the devices of this invention completely enclose all the chemicals and materials they use, so that no corrosive materials, e.g., a liquid solution of a fiber, particle or deliquescent salt, can leak from the device. For example, materials like blotter paper or silica particles do not involve leakage potential, such as is present in many disposable humidity measuring devices. The product stored in a package with the HDI will not be contaminated by the detector or its component materials. Materials such as paper sometimes shed fibers and lint. Silica involves the presence of tiny particles. Such particles, fibers and lint may damage products that are sensitive to dust, such as electronic components. Accordingly, the HDI of the present invention resolves the problems that exist with conventional HDI devices.

The HDI device of the invention in one aspect gives a quantitative indication of the exposure dose to humidity by the simple expedient of observing the length of a colored stain, and does not use any dyes or deliquescent materials.

The detector device of the present invention is based on the principle that the dosimetry of water vapor is determinable by the flux of its diffusion through an opening into a passage that contains, or is in equilibrium with another passage, chamber or other structure that contains, chromogenic material. Water vapor is absorbed very rapidly onto the surface of solid particles as it diffuses and forms a nano-thin aqueous layer that partially dissolves some of the solid or of a coating on the solid surface. When a second solid coated with a chromogen is in intimate contact with the first solid, a chromogenic reaction takes place, which produces a visible color change. The length of the resulting color stain that is formed provides an indication of the integrated exposure dose. The chromophoric reaction may produce a fluorescent or phosphorescent product that can be measured electronically to produce a humidity exposure dose indication.

The term "color change" as used herein is intended to be construed broadly and to include all forms of change including fluorescence, phosphorescence, etc. Regardless if the measure of the stain length involves measuring colors, fluorescence or other properties of the stain, the quantitative indication is obtained by measuring the stain length.

The shape or the cross-section of the conduit used in the dosimeter of the invention may vary and in specific embodiments includes rectangular, circular, triangular etc. designs. The cross-section of the conduit may be uniform or variable. The design of the conduit may also vary and include straight or spiral forms or conduits of different other shapes. Any shape or cross-section that permits water vapors to diffuse through it may be used in specific applications.

Moreover, the entire length of the conduit, or only a selected part of it, may contain the chromogenic mixture, depending on the objectives of the device.

A scale or other measuring indicia or information may be printed on the outer side of the dosimeter with numerical dose values, to facilitate the understanding of the information provided by the device in use, and the quantitative nature of the device, for dosimetry measurement.

The present invention relates in one aspect to an irreversible humidity exposure dose indicator device, comprising:

an elongate housing sealed at a first end thereof and adapted at a second end thereof to admit ambient gas ingress into an interior volume of the housing; and chromogenic material in said interior volume that upon contact with water irreversibly absorbs such water to produce a change in said chromogenic material yielding a quantity of changed chromogenic material whose extent is correlative of cumulative exposure of the device to humidity.

In another aspect, the invention relates to an HDI indicator card including a permeable membrane coated on a first side thereof with a layer of a deliquescent solid and in contact on a second side thereof with a layer containing a reactive indicator, with a water-permeable layer adjacent to the layer containing the deliquescent coating, and with all layers and membrane being enclosed within a water-impermeable transparent enclosure, wherein the enclosure includes an opening to the water-permeable layer, and the opening is shielded by a removable member that is removed to permit water vapor to diffuse through the opening and liquefy the deliquescent material, so that the liquid permeates through the membrane to interact with the reactive indicator and produce a color change indicative of cumulative humidity exposure of the indicator card.

Such HDI indicator card may have a scale on the enclosure to enable a viewer to observe progress of the color change indicative of cumulative humidity exposure of the indicator card.

Another aspect of the invention relates to a method of monitoring cumulative humidity exposure of a locus susceptible to presence or incursion of moisture, by providing at such locus an HDI device as described herein, and periodically determining from such device a cumulative humidity exposure of the locus.

Other aspects, features and embodiments of the invention will be more fully apparent from the ensuing disclosure and appended claims.

DETAILED DESCRIPTION OF THE INVENTION

Figure 1:
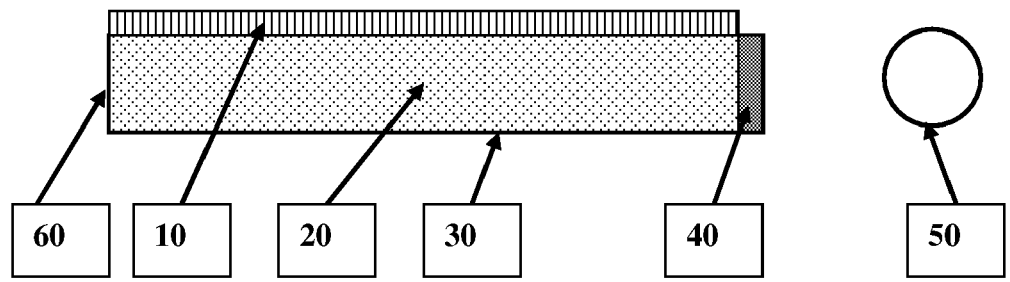
FIG. 1 is a schematic representation of an HDI according to one embodiment of the invention.

The present invention utilizes three basic phenomena in the provision of a new class of HDI devices:

1. Diffusion of materials like water vapor through air or other materials. The one-dimensional diffusion of water vapor can be approximated by Ficke's Law:

$$F=-D*dc/dx \qquad (2)$$

where F is the flux of the diffusing water vapor, D is its diffusivity coefficient, c is the concentration of the diffusing water vapor, and x the length coordinate in the direction of diffusion.

2. Irreversible sorption of water vapors on surfaces of certain solids and the subsequent dissolution of some of the material on the solid surface.

3. Chromogenic reaction of between nano-thin layers of solutions on the surface of one material and materials on the surface of other solids in intimate contact with it.

The invention in a broad aspect relates to an irreversible humidity exposure dose indicator device, comprising:

an elongate housing sealed at a first end thereof and adapted at a second end thereof to admit ambient gas ingress into an interior volume of the housing; and chromogenic material in the interior volume that upon contact with water irreversibly absorbs such water to produce a change in the chromogenic material yielding a quantity of changed chromogenic material whose extent is correlative of cumulative exposure of the device to humidity.

In such device, the second end comprises an opening that may be open, if of sufficiently small dimensions, or may alternatively have a porous humidity-permeable plug therein. The change in the chromogenic material can be of a simple type, e.g., a color change, and the extent of the changed chromogenic material can be demarcated by a wavefront of color change that is readily visually correlated to cumulative exposure of the device to humidity.

The elongate housing can have any suitable shape, e.g., a circular cross-section, a rectangular cross-section, a triangular cross-section, etc. The elongate housing in one embodiment comprises a conduit. In order to visually detect the presence of the wavefront or other extent of changed chromogenic material attributable to moisture exposure, at least a portion of the elongate housing may be formed of a transparent material, such as glass or a transparent polymer.

The HDI device of the invention can be fabricated with a scale that is at least partially coextensive with a length dimension of the elongate housing, to facilitate determination of the cumulative humidity exposure of the device from the scale. The scale may be provided as a separate scale member that is affixed or secured to the housing. The scale may have indicia of cumulative humidity exposure of the device, such as numeric scale values of cumulative humidity, printed or embossed on the housing. By such scale arrangement, the extent of changed chromogenic material in the housing can be correlated to a cumulative humidity exposure and read from the scale, or a scale value can be cross-indexed to a chart of cumulative humidity dosage so that a value read from the scale on the housing is used to determine a "chart value" of cumulative humidity exposure.

The porous humidity-permeable plug that may be provided at the opening of the housing of the HDI device can be formed of any suitable material, such as materials selected from among, fabrics, natural fibers, cotton, cellulose, polymeric fibers, glass fibers, ceramic fibers, polyethylene fibers, polypropylene fibers, polyurethane fibers, polyester fibers, fluoropolymer fibers, ceramic membranes, polymeric membranes, glass membranes, metallic mesh, and sintered metallic particles.

The chromogenic material in the housing can be of any appropriate fill amount in the interior volume of the housing. For example, the chromogenic material may fill the entire cross-section of the housing or only a portion of the cross section of the housing.

The change in the chromogenic material in the housing can be of any suitable type that is perceptible to indicate the cumulative humidity exposure, such as irreversible color change, irreversible fluorescence, or irreversible phosphorescence.

The chromogenic material itself is suitable of a particulate form, comprising chromogenic particles. The particles in turn can be of any suitable type, e.g., particles having a reactive surface, particles having a chromogenic coating, particles containing reactive materials, particles devoid of reactive materials within them, particles comprising a mixture of different materials, polymeric particles, silica particles, alumina particles, thoria particles, lanthanum oxide particles, titanium oxide particles, sintered metal oxide particles, magnesium particles, zinc oxide particles, diatomaceous earth particles, etc.

The particles can be of any suitable sizes and size distribution. In one embodiment, the particles are 0.02 to 500 μm in size.

The chromogenic material in another embodiment comprises particles including a mixture of a hydrolysable material and a second material that is chromogenically reactive with hydrolyzed material deriving from the hydrolyzable material when contacted with water. The hydrolyzed material can for example produce metallic ions that are chromogenically reactive with a chromophore specific to the ions, e.g., metallic ions including a metal such as nickel, cadmium, zinc, cobalt, copper, iron, lead, or other ions reactive with water.

In a specific embodiment, the chromophore can include ditizon (3-anilino-1-phenylimino-thiourea), rubeanic acid (1,2-diiminoethane-1,2-dithiol), di-methyl-glyoxime (N-(3-nitrosobut-2-en-2-yl)hydroxylamine), copperon (N-nitroso-N-phenyl-hydroxylamine), zincon (2-[(2-hydroxy-5-sulfo-phenyl)aminoimino-phenyl-methyl]diazenylbenzoic)acid, arsenazo, 1,1'-dipyridyl, PAN 1-(2-Pyridylazo)-2-naphthol) or PAR (4-pyridin-2-yldiazenylbenzene-1,3-diol).

In one specific embodiment, the chromogenic material employed in the HDI device comprises a nickel hydroxy oxide having the formula NiOx(OH)y wherein 2x+y=2. In another embodiment, the chromogenic material comprises porous silica particles having dimethyl glyoxime deposited thereon at a concentration in a range of from 1 mg/gram to 500 mg/gram, with the particles having a diameter in a range of from about 0.02 to 200 μm.

In other embodiments, the HDI device has different ratios of various solids in the chromogenic material, to adjust the HDI sensitivity, and/or different surface treatments of the solids in the chromogenic material.

The HDI device can have an overall configuration of any suitable type. For example, the device can include a transparent housing that is tube-shaped, with graduated markings on the outside surface so that the cumulative humidity dose is easily read from the device by visual inspection of same to determine the linear distance of the calorimetric change in the contained chromogenic material.

In another embodiment, the housing containing the chromogenic material can be provided in the form of a card or strip of a transparent or translucent material that permits determination of the cumulative humidity exposure by the length of the card or strip that has changed color, as the chromogenic material undergoes color change in contact with ambient moisture, with a changed color wavefront propagating from an opening, e.g., an edge opening allowing ingress of ambient moisture, along the length of the card or strip toward an opposite closed end thereof.

In a specific implementation, the HDI device is configured as an indicator card including an intermediate permeable membrane coated on a first side thereof with a layer of a deliquescent solid and being in contact on a second side thereof with a layer containing a reactive indicator, with a water-permeable layer adjacent to the layer containing the deliquescent coating, and with all layers being enclosed within a water-impermeable transparent enclosure. The device can include an opening to the permeable layer that is shielded by a removable member that is removed to initiate the dosimetric process, and permit water vapor to diffuse through the opening and liquefy the deliquescent material, so that the liquid permeates through the membrane and a visible indication of the location of the wet front is seen as the water contacts the chromogenic material. A scale can be printed on the exterior of the enclosure to permit a viewer to see the progress of the indication, e, g. of a color front, to thereby determine the cumulative humidity exposure of the device.

Cards of such type can be readily fabricated without undue experimentation, based on the disclosure herein.

The device in use can be disposed in a container or other location that is susceptible to the presence or incursion of moisture, so that a ready visual determination can be made of the cumulative moisture exposure of the device in such container or other location.

Referring now to the drawings, FIG. 1 is a schematic representation of an HDI with a circular cross-section based on a capillary tube. A scale 10 is attached to the conduit 30 filled with the chromophore 20 and the tube is sealed by a closed end 60, with an open end of the tube containing a porous plug 40 that permits ingress of water vapor into the interior volume of the tube, for calorimetric interaction with the chromophore 20 therein. A circular cross-section 50 of the conduit is shown in the end elevation view at the right-hand portion of FIG. 1. In operation, water vapor diffuses through the porous plug and effects a color change in interaction with the chromophore, to create a differently colored wavefront that progresses toward the closed end of the conduit, to show the progressive, cumulative humidity dose. For this purpose, the scale 10 is calibrated to provide a reading showing the cumulative water vapor exposure.

Figure 2:
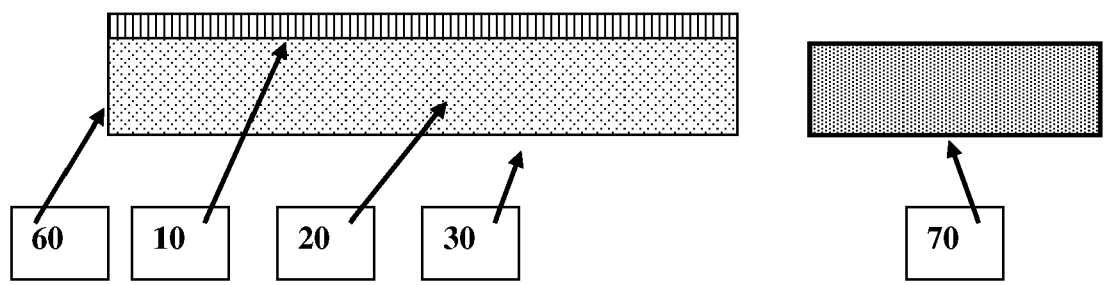
FIG. 2 is a schematic representation of an HDI according to another embodiment of the invention.

FIG. 2 is a schematic representation of an HDI having a rectangular cross-section based on a plastic laminate. A graduated scale 10 is attached to the conduit 30 filled with the chromophore 20, and sealed at closed end 60. A rectangular cross-section 70 of the conduit is shown in the end elevation view at the right-hand portion of FIG. 2. In contrast to the HDI of FIG. 1, the HDI of FIG. 2 contains no porous end plug, and is merely open at its right-hand end as depicted in FIG. 2. In general, a porous plug may be eliminated from the HDI if the opening for ingress of water vapor is sufficiently narrow. In operation, water vapor diffuses into the interior volume of the conduit 30 and effects a color change in interaction with the chromophore, to create a differently colored (relative to the chromophore material unexposed to any moisture) wavefront that progresses toward the closed end of the conduit, to show the progressive, cumulative humidity dose. For this purpose, the scale 10 is calibrated to provide a reading showing the cumulative water vapor exposure.

Figure 3:
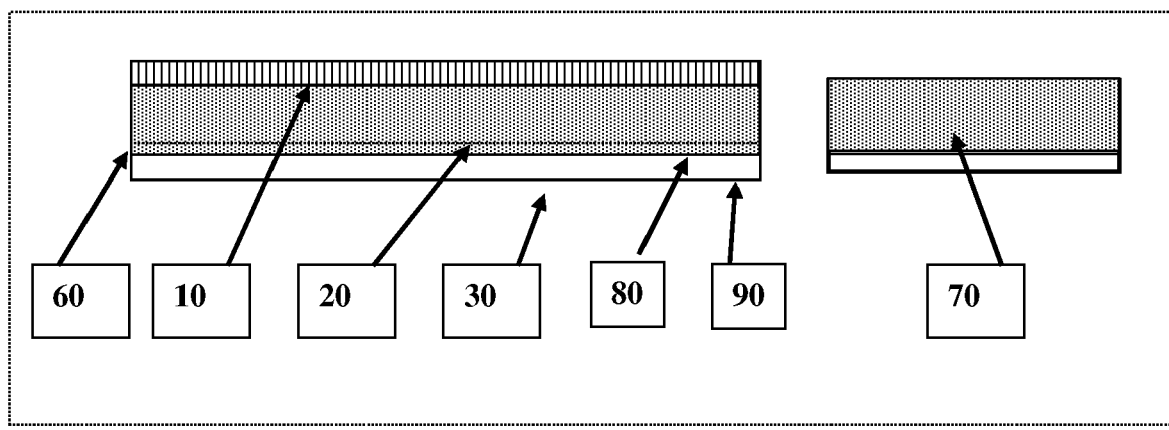
FIG. 3 is a schematic representation of an HDI according to yet another embodiment of the invention.

FIG. 3 is a schematic representation of an HDI with a rectangular cross-section divided into two compartmental regions by a membrane. The first region is filled with a chromophore 20, and is separated from the second compartmental region 90 (gap region) by the membrane 80. The conduit 30 has a scale 10 attached thereto with graduated indicia providing a quantitative visual output of the cumulative humidity exposure, by reading of the scale at the wavefront, as such differently colored wavefront progresses from the open end toward the closed end 60 of the conduit with continuing humidity exposure. A rectangular cross-section 70 of the conduit is shown in the end elevation view at the right-hand portion of FIG. 3. In this embodiment, the right-hand end of the conduit is open, and in contrast to the HDI of FIG. 1, contains no porous plug or other occlusion, simply being open to accommodate diffusional ingress of moisture from the ambient environment into the interior volume of the conduit for calorimetric interaction with the chromophoric medium therein.

It will be recognized that any of the HDI devices illustratively described in connection with FIGS. 1-3 hereof may be modified to include a calorimetric sensor assembly that is arranged and adapted to determine the cumulative humidity exposure, by correlation of the position of the wavefront in the mass of chromophore material, as such wavefront travels through the elongated body of chromophoric medium. For example, a light or other radiation signal may be impinged on the body of chromophoric medium, and a corresponding reflected or transmitted signal may be employed to determine the specific location of the wavefront, and correspondingly the quantitative value of the cumulative humidity exposure.

The features and advantages of the invention are more fully apparent from the ensuing illustrative examples, which are not intended to be limiting, as regards the scope and applicability of the invention.

EXAMPLE 1

A Capillary Humidity Dosimeter

Figure 4:
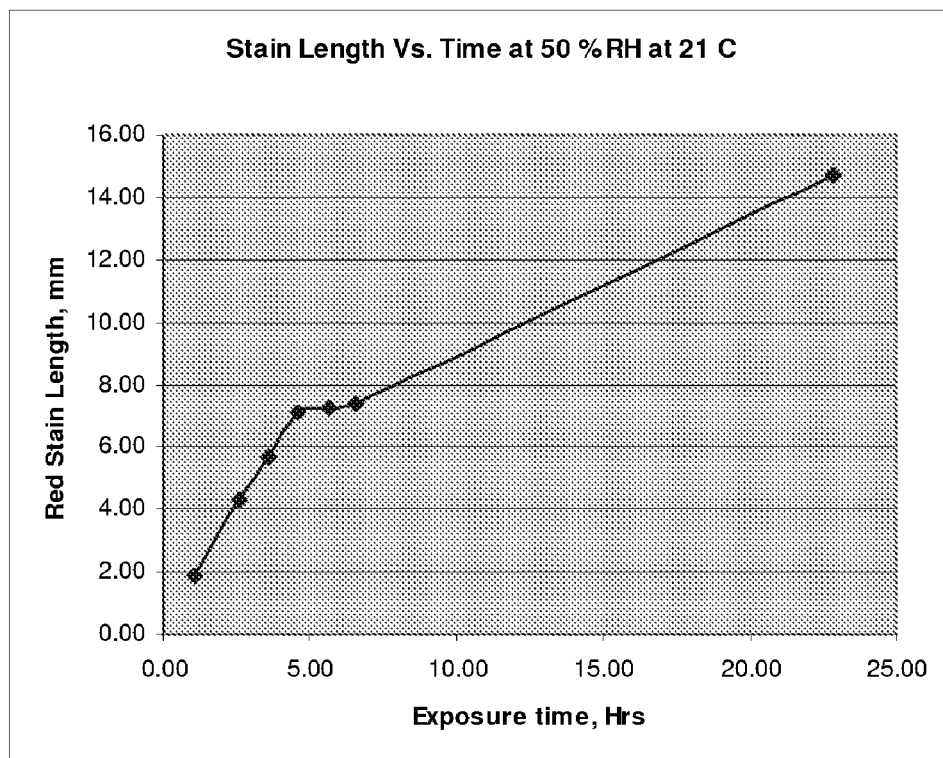
FIG. 4 is a graph of red stain length, in millimeters, as a function of exposure time, in hours, at 50% relative humidity and 21° C., for an HDI device according to one embodiment of the invention.

An HDI was prepared using a glass capillary 90 mm long and having an 1.8 mm OD, and a 1 mm ID, by filling it with a 50×50% wt of 63-200 microns silica gel having a BET surface area of about 300 m$^2$/gm, coated by dimethyl glyoxime at 33 mg/gm; and nickel hydroxy-oxide powder of comparable particle size dried 2 hours at 150° C. A 1 mm long plug of glass wool was used to close the capillary open end. These dosimeters were exposed to static air with fixed relative humidity of 50% at 21° C., and the length of the red stain formed as a result of the exposure to the humidity was measured, in millimeters, as a function of time, in hours, yielding the curve shown in the graph of FIG. 4.

EXAMPLES 2-6

A Capillary Humidity Dosimeter with Variable Ratios of Nickel to Silica

Dosimeters were prepared as described in Example No. 1 but the amount of nickel hydroxy-oxide was varied in the range of 10% to 90%. The results are shown in FIG. 5, which is a graph of length of the color stain, in millimeters, as a function of percent nickel in the chromophoric medium, at various exposure times (2 hrs, 4 hrs, 6.18 hrs, 8 hrs and 24 hrs).

Figure 5:
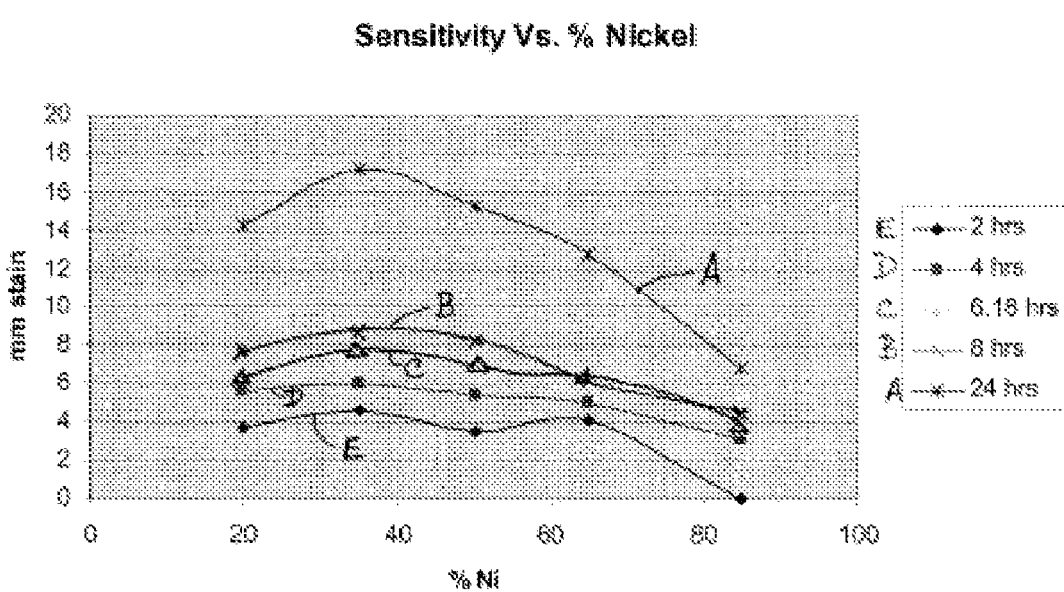
FIG. 5 is a graph of length of the color stain, in millimeters, as a function of percent nickel in the chromophoric medium, for HDI devices in accordance with the invention, in which the nickel concentration was varied in a range of from 10 to 90%.

The data in FIG. 5 show that the greatest sensitivity is obtained when the nickel hydroxy oxide concentration is about 35%.

EXAMPLES 7-14

The Performance of the Capillary Humidity Dosimeter at Different Fixed RH Values at 21° C.

Figure 6:
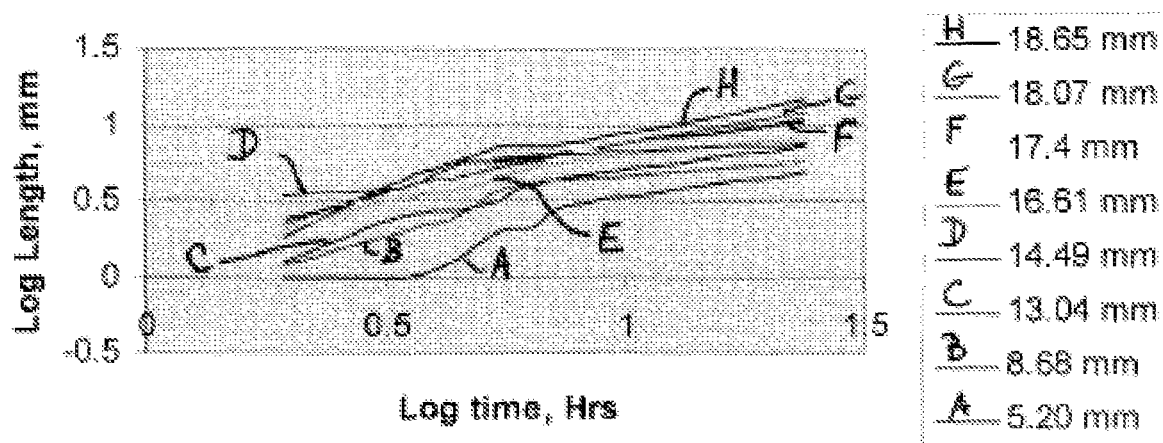
FIG. 6 is a graph of the logarithm of stain length, in millimeters, as a function of the logarithm of exposure time, in hours, at 21° C., for water vapor pressures of varying values, for an HDI device in accordance with the invention.

The length of the stain formed in the HDI of Example 1 was tested at fixed water vapor pressures. The data are shown in FIG. 6, which is a graph of the logarithm of stain length, in millimeters, as a function of the logarithm of exposure time, in hours, at 21° C., for water vapor pressure of 5.20 mm, 8.68 mm, 13.04 mm, 14.49 mm, 16.61 mm, 17.4 mm, 18.07 mm, and 18.65 mm.

While the invention has been illustratively described herein with reference to specific aspects, features and embodiments, it will be apparent that the invention is not thus limited, but rather extends to and encompasses variations, modifications and other embodiments, as will readily suggest themselves to those of ordinary skill in the art, based on the disclosure herein. Accordingly, the invention is intended to be broadly construed, as encompassing such variations, modifications and alternative embodiments, within the spirit and scope of the claims as hereinafter set forth.

What is claimed is:

1. An irreversible humidity exposure dose indicator device, comprising:
   an elongate housing sealed at a first end thereof and adapted at a second end thereof to admit ambient gas ingress into an interior volume of the housing; and
   chromogenic material in said interior volume that upon contact with water irreversibly absorbs such water to produce a change in said chromogenic material yielding a quantity of changed chromogenic material whose extent is correlative of cumulative exposure of the device to humidity.

2. The device of claim 1, wherein said second end comprises an opening.

3. The device of claim 1, wherein said second end has a porous humidity-permeable plug therein.

4. The device of claim 1, wherein said change in said chromogenic material comprises a color change.

5. The device of claim 1, wherein said extent of said changed chromogenic material is demarcated by a wavefront of color change.

6. The device of claim 1, wherein said elongate housing has a circular cross-section.

7. The device of claim 1, wherein said elongate housing has a rectangular cross-section.

8. The device of claim 1, wherein said elongate housing comprises a conduit.

9. The device of claim 1, wherein at least a portion of said elongate housing is formed of a transparent material.

10. The device of claim 9, wherein said transparent material is selected from the group consisting of glass and transparent polymers.

11. The device of claim 1, wherein said elongate housing as a cross-section of a shape selected from the group consisting of rectangular, triangular and circular shapes.

12. The device of claim 1, further comprising a scale at least partially coextensive with a length dimension of said elongate housing, said scale having indicia of cumulative humidity exposure of the device, so that the extent of changed chromogenic material in said elongate housing can be correlated to a cumulative humidity exposure from said scale.

13. The device of claim 12, wherein said scale indicia are printed on the housing.

14. The device of claim 12, wherein said scale comprises a scale member affixed to said elongate housing.

15. The device of claim 3, wherein said porous humidity-permeable plug comprises a material selected from the group consisting of fabrics, natural fibers, cotton, cellulose, polymeric fibers, glass fibers, ceramic fibers, polyethylene fibers, polypropylene fibers, polyurethane fibers, polyester fibers, fluoropolymer fibers, ceramic membranes, polymeric membranes, glass membranes, metallic mesh, and sintered metallic particles.

16. The device of claim 1, wherein the entire cross-section of the elongate housing is filled with the chromogenic material.

17. The device of claim 1, wherein only a portion of the cross section of the elongate housing is filled with the chromogenic material.

18. The device of claim 1, wherein the change in said chromogenic material comprises a change selected from the group consisting of irreversible color change, irreversible fluorescence, and irreversible phosphorescence.

19. The device of claim 1, wherein the chromogenic material comprises chromogenic particles.

20. The device of claim 19, wherein said chromogenic particles comprise particles selected from the group consisting of particles having a reactive surface, particles having a chromogenic coating, particles containing reactive materials, particles devoid of reactive materials within them, particles comprising a mixture of different materials, polymeric particles, silica particles, alumina particles, thoria particles, lanthanum oxide particles, titanium oxide particles, sintered metal oxide particles, magnesium particles, zinc oxide particles, diatomaceous earth particles.

21. The device of claim 19, wherein said chromogenic particles are 0.02 to 500 μm in size.

22. The device of claim 1, where the chromogenic material comprises particles including a mixture of a hydrolyzable material and a second material that is chromogenically reactive with hydrolyzed material deriving from the hydrolyzable material when contacted with water.

23. The device of claim 22, wherein said hydrolyzed material produces metallic ions that are chromogenically reactive with a chromophore specific to said ions.

24. The device of claim 23, wherein said metallic ions comprise metal selected from the group consisting of nickel, cadmium, zinc, cobalt, copper, iron, lead, and other ions reactive with water.

25. An irreversible humidity exposure dose indicator device, comprising:
   an elongate housing sealed at a first end thereof and adapted at a second end thereof to admit ambient gas ingress into an interior volume of the housing; and
   chromogenic material in said interior volume that upon contact with water irreversibly absorbs such water to produce a change in said chromogenic material yielding a quantity of changed chromogenic material whose extent is correlative of cumulative exposure of the device to humidity,
   wherein the chromogenic material comprises particles including a mixture of a hydrolyzable material and a second material that is chromogenically reactive with hydrolyzed material deriving from the hydrolyzable material when contacted with water,
   wherein said hydrolyzed material produces metallic ions that are chromogenically reactive with a chromophore specific to said ions,
   wherein said chromophore is selected from the group consisting of ditizon, rubeanic acid, di-methyl-glyoxime, copperon, zincon, arsenazo, 1,1'dipyridyl, PAN and PAR.

26. The device of claim 1, wherein the chromogenic material comprises a nickel hydroxy oxide having the formula $NiO_x(OH)_y$ wherein $2x+y=2$.

27. The device of claim 1, wherein the chromogenic material comprises porous silica particles having dimethyl glyoxime deposited thereon at a concentration in a range of from 1 mg/gram to 500 mg/gram, said particles having a diameter in a range of from about 0.02 to 200 μm.

28. A method of monitoring cumulative humidity exposure of a locus susceptible to presence or incursion of moisture, comprising providing at said locus a device according to claim 1, and periodically determining from said device a cumulative humidity exposure of said locus.

* * * * *